United States Patent [19]

Kang et al.

[11] Patent Number: 5,656,448
[45] Date of Patent: Aug. 12, 1997

[54] DIPSTICK IMMUNOASSAY DEVICE

[75] Inventors: Jemo Kang, Princeton; John A. Colanduoni, Bridgewater, both of N.J.; Dong Joon Lee, Seoul, Rep. of Korea; Byungwoo Youn, Wyckoff, N.J.; Chiyoung Ok, Seoul, Rep. of Korea; Walter J. Kang, Princeton, N.J.

[73] Assignee: Princeton Biomeditech Corporation, Princeton, N.J.

[21] Appl. No.: 182,512

[22] Filed: Jan. 14, 1994

Related U.S. Application Data

[63] Continuation of Ser. No. 462,828, Jan. 10, 1990, abandoned.

[51] Int. Cl.$^6$ .................... G01N 33/53; G01N 33/548
[52] U.S. Cl. .................... 435/7.94; 422/56; 422/57; 435/7.9; 435/7.92; 435/21; 435/26; 435/28; 435/962; 435/963; 435/970; 435/975; 435/287.2; 435/287.7; 435/805; 435/810; 436/518; 436/527; 436/530; 436/531; 436/169; 436/808; 436/810
[58] Field of Search .................... 422/56, 57; 435/7.9, 435/7.92–7.95, 18, 21, 25–26, 28, 962, 963, 970, 975, 287.1, 287.2, 287.7, 805, 810; 436/518, 527, 530, 531, 808, 810, 169

[56] References Cited

U.S. PATENT DOCUMENTS

| | | | |
|---|---|---|---|
| 4,038,485 | 7/1977 | Johnston et al. | 436/810 X |
| 4,090,888 | 5/1978 | Rademachers et al. | 106/304 |
| 4,168,146 | 9/1979 | Grubb et al. | 422/56 X |
| 4,361,537 | 11/1982 | Deutsch et al. | 422/56 |
| 4,373,932 | 2/1983 | Gribnau et al. | 436/501 |
| 4,376,110 | 3/1983 | David et al. | 436/518 |
| 4,435,504 | 3/1984 | Zuk et al. | 436/530 X |
| 4,632,901 | 12/1986 | Valkirs et al. | 436/805 X |
| 4,740,468 | 4/1988 | Weng et al. | 436/530 X |

(List continued on next page.)

FOREIGN PATENT DOCUMENTS

| | | |
|---|---|---|
| 0 125 118 | 11/1984 | European Pat. Off. |
| 0143574 | 6/1985 | European Pat. Off. |
| 0164194 | 12/1985 | European Pat. Off. |
| 0186100 | 7/1986 | European Pat. Off. |
| 0100619 | 8/1986 | European Pat. Off. |
| 0191640 | 8/1986 | European Pat. Off. |
| 0202081 | 11/1986 | European Pat. Off. |
| 0250137 | 12/1987 | European Pat. Off. |
| 0253579 | 1/1988 | European Pat. Off. |
| 0279097 | 8/1988 | European Pat. Off. |
| 0 282 192 | 9/1988 | European Pat. Off. |
| 0296724 | 12/1988 | European Pat. Off. |
| 0298368 | 1/1989 | European Pat. Off. |
| 0299299 | 1/1989 | European Pat. Off. |
| 0305536 | 3/1989 | European Pat. Off. |
| 0306336 | 3/1989 | European Pat. Off. |
| 0306772 | 3/1989 | European Pat. Off. |
| 84/04171 | 11/1984 | WIPO |
| 88/08536 | 11/1988 | WIPO |
| 88/09824 | 12/1988 | WIPO |

*Primary Examiner*—James C. Housel
*Assistant Examiner*—Susan C. Wolski

[57] ABSTRACT

The invention pertains to dipstick immunoassay devices. The device comprises a base member and a single, combined sample contact zone and test zone, wherein the test zone incorporates the use of symbols to detect analytes in a sample of biological fluid. A first immunological component, an anti-immunoglobulin capable of binding to an enzyme-labeled antibody, is immobilized in a control indicia portion. A second immunological component, capable of specifically binding to a target analyte which is bound to the enzyme-labeled antibody to form a sandwich complex, is immobilized in a test indicia portion. The enzyme-labeled antibody produces a visual color differential between a control indicia portion and a non-indicia portion in the test zone upon contact with a substrate. The device additionally includes a first polyol and a color differential enhancing component selected from the group consisting of an inhibitor to the enzyme and a competitive secondary substrate for the enzyme distributed throughout the non-indicia portion of the test zone.

26 Claims, 1 Drawing Sheet

U.S. PATENT DOCUMENTS

| | | | |
|---|---|---|---|
| 4,748,115 | 5/1988 | Steaffens et al. | 435/4 X |
| 4,757,004 | 7/1988 | Houts et al. | 436/528 X |
| 4,780,422 | 10/1988 | Mitani et al. | 436/524 |
| 4,786,589 | 11/1988 | Rounds | 435/805 X |
| 4,786,594 | 11/1988 | Khanna et al. | 435/805 X |
| 4,786,606 | 11/1988 | Giegel et al. | 436/514 X |
| 4,790,979 | 12/1988 | Terminiello et al. | 422/56 |
| 4,837,395 | 6/1989 | Leeder et al. | 435/7.91 X |
| 4,853,335 | 8/1989 | Olsen et al. | 436/527 |
| 4,857,453 | 8/1989 | Ullman et al. | 435/7 |
| 4,859,612 | 8/1989 | Cole et al. | 436/523 |
| 4,959,307 | 9/1990 | Olsen | 422/56 X |
| 5,008,080 | 4/1991 | Brown, III et al. | 422/57 X |
| 5,030,558 | 7/1991 | Litman et al. | 435/970 X |
| 5,104,793 | 4/1992 | Buck | 435/963 X |
| 5,137,804 | 8/1992 | Greene et al. | 435/5 |

DIPSTICK IMMUNOASSAY DEVICE

This application is a continuation of application Ser. No. 07/462,828 filed on Jan. 10, 1990, now abandoned.

BACKGROUND OF THE INVENTION

Various methods for detecting the presence of an analyte in a sample of biological fluid through the use of immunochemistry have been described. In the so-called "sandwich" method, for example, a target analyte such as an antigen is "sandwiched" between a labeled antibody and an antibody immobilized onto a solid support. The assay is read by observing the presence and amount of antigen-labeled antibody complex bound to the immobilized antibody. In the competition immunoassay method, antibody bound to a solid surface is contacted with a sample containing both an unknown quantity of antigen analyte and with labeled antigen of the same type. The amount of labeled antigen bound on the solid surface is then determined to provide an indirect measure of the amount of antigen analyte in the sample.

Because these and other methods discussed below can detect both antibodies and antigens, they are generally referred to as immunochemical ligand-receptor assays or simply immunoassays.

Solid phase immunoassay devices, whether of the sandwich or competition type, provide sensitive detection of an analyte in a biological fluid sample such as blood or urine. Solid phase immunoassay devices incorporate a solid support to which one member of a ligand-receptor pair, usually an antibody, antigen, or hapten, is bound. Common early forms of solid supports were plates, tubes, or beads of polystyrene which were known from the fields of radioimmunoassay and enzyme immunoassay. More recently, a number of porous materials such as nylon, nitrocellulose, cellulose acetate, glass fibers, and other porous polymers have been employed as solid supports.

A number of self-contained immunoassay kits using porous materials as solid phase carriers of immunochemical components such as antigens, haptens, or antibodies have been described. These kits are usually dipstick, flow-through, or migratory in design.

Tom et al., U.S. Pat. No. 4,366,241, and Zuk, EP-A 0 143 574 describe migration type assays in which a membrane is impregnated with the reagents needed to perform the assay. An analyte detection zone is provided in which labeled analyte is bound and assay indicia is read.

Bernstein, U.S. Pat. No. 4,770,853, May et al., WO 88/08534, and Ching et al., EP-A 0 299 428 describe migration assay devices which incorporate within them reagents which have been attached to colored direct labels, thereby permitting visible detection of the assay results without addition of further substances.

Valkirs et al., U.S. Pat. No. 4,632,901, disclose a flow-through type immunoassay device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

Korom et al., EP-A 0 299 359, discloses a variation in the flow-through device in which the labeled antibody is incorporated into a membrane which acts as a reagent delivery system.

Baxter et al., EP-A 0 125 118, disclose a sandwich type dipstick immunoassay in which immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products which either deposit as a precipitate onto the solid phase or produce a visible color change in the substrate solution.

Kali et al., EP-A 0 282 192, disclose a dipstick device for use in competition type assays.

Leuvering in U.S. Pat. No. 4,313,734 describes the use of gold sol particles as a direct label in a dipstick device.

Rounds in U.S. Pat. No. 4,786,589 describes a dipstick immunoassay device in which the antibodies have been labeled with formazan.

The requirements for washing steps and extended enzyme substrate incubation periods with dipstick immunoassay devices using enzyme labeled antibodies increases variability and thus the likelihood that minimally trained personnel and home users will obtain erroneous assay results.

DETAILED DESCRIPTION

The present invention pertains to dipstick immunoassay devices. In particular, the present invention comprises an immunological dipstick device which incorporates the use of symbols in the test zone and enzyme labeled antibodies to detect analytes in a sample of biological fluid. The device obviates the need for the intermediate washing step associated with dipstick type enzyme labeled antibody assays.

Figure 1:
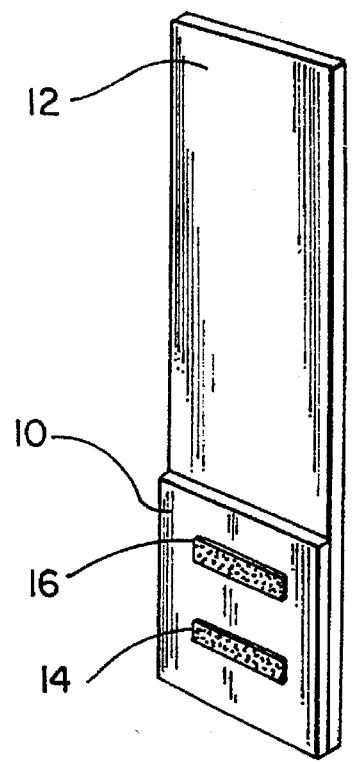
Figure 2:
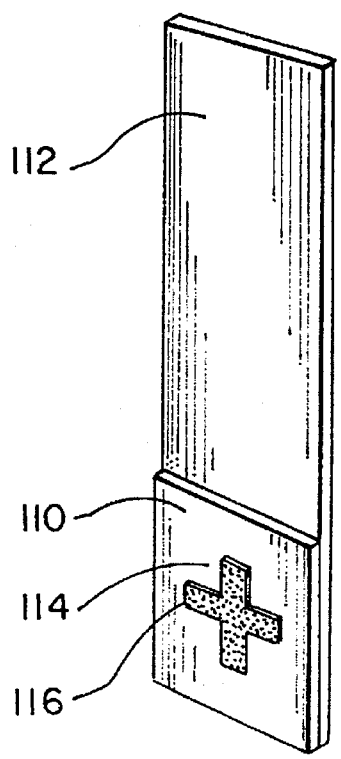

The nature of the invention will be apparent from the following description and from the accompanying drawing in which;

FIG. 1 is a perspective view of a typical dipstick device of the present invention showing assay and control indicia in the configuration of bars; and FIG. 2 is a perspective view of a further embodiment of a dipstick device according to the present invention showing assay and control indicia in the configuration of a plus (+) sign.

Referring now to FIG. 1, test zone 10 is defined on base member 12. Base member 12 is constructed from a strip of moisture impervious material which provides a rigid support for zone 10 in order to facilitate its movement between containers. Typical base materials include but are not limited to glass or any number of plastics. Zone 10 can be constructed from a variety of elements, examples of which include but are not limited to nylon, nitrocellulose, cellulose, cellulose acetate, fiberglass, polysulfone, polyvinylidene diflouride, and polyester. An immunological component is immobilized onto zone 10 in the configuration of indicia 14, here shown as a simple bar. The immunological component is operable to bind an enzyme-labeled antibody through a target analyte, thereby forming a sandwich complex extending above test zone 10. A second immunological component (anti-IgG) also is immobilized in the configuration of control indicia 16, again shown as a bar. Control indicia 16 acts as an internal monitor with which to gauge assay completion.

The methods by which the antibodies are labeled with enzymes are well known in the art, as is the chemistry by which these labels cause insoluble colored products to precipitate out of solution when brought into contact with the appropriate substrate solution.

In use, test zone 10 is inserted into a container of fluid sample to which enzyme labeled anti-analyte antibody has been added. This is allowed to stand for a short time (as for example 3–4 minutes) during which time target analyte, if present, binds to the immunological component immobilized in indicia 14 and labeled antibody binds to the analyte to form a plurality of "sandwich" complexes extending above test zone 10 along indicia 14. A portion of the labeled antibody which does not bind to the target analyte binds to the anti-immunoglobin G immobilized in control indicia 16. The dipstick is removed from the first container and inserted into a second containing enzyme substrate. Upon contact with substrate, the enzyme labels presently extending above test zone 10 act to liberate insoluble colored products which deposit along indicia 14 and control indicia 16 in higher concentrations than in non-indicia areas of test zone 10. This results (i) in both a visible colored band in indicia 14 and in control indicia 16 if analyte is present or (ii) in only a single visible colored band in control indicia 16 if no analyte is present.

In a further embodiment of the present invention the concentration of substance immobilized in control indicia 16 is calibrated so as to provide an internal gauge of the concentration of analyte in a sample. For example, substance is immobilized in indicia 16 at a given concentration and the assay is completed. If the color that appears in indicia zone 14 is darker than that which appears in control indicia 16, the sample contains target analyte at a greater concentration than the given concentration.

Alternatively, as shown in FIG. 2, a vertical indicia 114 is situated perpendicular to and overlapping control indicia 116 on test zone 110 in the configuration of a plus (+) sign. Operationally, the device is used in the same manner as that described for FIG. 1; now however a colored plus (+) sign becomes visible on zone 110 in the presence of target analyte, whereas if no target analyte is present a colored minus (–) sign appears.

Immunological substance can be immobilized on the test zone in any configuration which is practical or easily discernable. These configurations include but are not limited to, dots, bars, letter, numbers, and plus-minus signs. The plus-minus configuration in which anti-analyte antibody or antigen specific to a target antibody is immobilized perpendicular to a horizontal control bar of anti-Immunoglobin provides simplicity in interpreting assay results for home users since the appearance of a plus (+) sign indicates a positive result and a minus (–) sign indicates a negative result.

Printing or spraying an immunological component onto the test zone in a defined configuration provides an internal color differential on the test zone of the dipstick itself so that additional standard color charts are not needed in order to interpret assay results. In addition no washing is needed before the device is brought into contact with substrate solution. The colored substances generated deposit in greater numbers along the indicia configuration than in non-indicia areas of the test zone. Therefore washing to remove enzyme labeled antibody which has not been linked to the test zone through a target analyte is not needed.

Any number of enzymes can be used to label the antibodies. Typical enzymes include, but are not limited to alkaline phosphatase, horseradish peroxidase, lysozyme, glucose-6-phosphate dehydrogenase, lactate dehydrogenase, urease, glucose oxidase, β-Galactisidose, and cholesterol oxidase, with alkaline phoshatase being preferred.

Normally, once an assay has been completed the color differential generated between indicia and non-indicia areas on the test zone is great enough to provide an accurate indication of the presence or absence of a given analyte in a sample. However, this color differential can be enhanced by incorporating an enzyme inhibitor or competitive secondary substrate into non-indicia areas of the test zone membrane. Substances which exhibit relatively weak inhibitory behavior are preferred in order to avoid unwanted inhibition of those enzymes extending above the indicia areas. In those devices employing alkaline phophatase labeled antibodies, typical inhibitors include, but are not limited to, amino acids and their derivatives such as cysteine, histidine, L-phenylananine, β-phenyl-β-alanine, p-flourophenylalanine, and tyrosine; chelating agents such as ethylenediamine tetraacetic acid; complex oxygenated anions such as citrate, borate, arsenate, phosphate, orthophosphate, carbonate, polyestradiol phosphate, pyrophosphate, and polyphloretin phosphate; or halogenated carboxylic acid derivatives such as iodobenzoate and iodoacetamide; typical color generating competitive secondary substrates include p-nitrophenyl phosphate. Of the forgoing examples p-nitrophenyl phosphate is preferred.

When a test zone membrane which has p-nitrophenyl phosphate incorporated within non-indicia areas is brought into contact with alkaline phophatase labeled antibodies, insoluble yellow colored products are formed as phosphate ions are cleaved. These deposit on the test zone surface in non-indicia areas, while insoluble products (usually blue in color) which result from enzyme interactions involving the primary substrate deposit along indicia areas. Blue colored products which may deposit on non-indicia areas are masked by the yellow color.

In yet another embodiment, a first polyol is included with the enzyme inhibitor on the test zone in non-indicia areas. When alkaline phosphatase is used as an enzyme label, the polyol acts to accept phosphate ions generated as a result of enzyme-substrate interactions This feature serves two functions.

Firstly, by coating the membrane with phosphate ions the polyol renders the membrane surface hydrophilic and therefore repellant to the hydrophobic colored products which are generated as a result of enzyme substrate contact. Since the colored products are less likely to deposit on the membrane surface a greater color differential between indicia and non-indicia areas is thereby produced.

Secondly, by acting to accept the phosphates generated, the polyol increases the rate of reaction between the alkaline phosphatase and its substrate which in turn reduces the amount of time needed to incubate the dipstick in the substrate solution. Thus, more immediate assay results are possible. Examples of polyols which may be used include but are not limited to polyvinylalcohol, polyethylene glycol, sorbitol, polypropylene glycol, and carbohydrates such as dextran, methyl cellulose, milk, and corn starch. Of the forgoing examples polyvinylalcohol is preferred.

In instances where alkaline phosphatase is not used to label the antibodies, a substance which accepts by-products of the enzyme substrate reaction thereby rendering the membrane surface repellant to the deposition of insoluble colored product and/or decreases enzyme substrate incubation periods can be incorporated onto the membrane surface.

The present invention also includes a kit in which the dipstick device is combined with a solution of enzyme labeled antibody, and a second solution of enzyme substrate which is operable to form insoluble colored products upon contact with the enzyme label. The nature of the substrate will depend upon the particular enzyme used as a label.

When for example the antibodies have been labeled with alkaline phosphatase, examples of typical substrate solutions include but are not limited to Napthol AS-MX phosphate and Fast Blue RR salt, Napthol AS-MX phosphate and Fast Violet B Salt, Napthol AS-GR phosphate and Fast Blue RR Salt, 5-bromo-4-chloro-3-indolyl phosphate (BCIP), and 3-indoxyl phosphate. When horseradish peroxidase has been used as an enzyme label typical substrate solutions include, but are not limited to, 2,2'-azino-di-3-ethylbenzthiazidine sulfonate, 3,3',5,5'-tetramethylbenzidine, 4-chloro-1-napthal, 3,3'-diaminobenzidine, p-phenylenediamine and pyrocatechol, 3-amino-9-ethylcarbazole, and napthal/pyronine. Examples of a typical substrate solution for a lactate dehydrogenase label include, but are not limited to, reduced nicotinamide adenine dinucleotide (NADH), and phenazine methosulphate and nitroblue tetrazolium. When antibodies are labeled with lipozyme, a typical substrate solution comprises insoluble colored substances which have been encapsulated within liposomes. A typical substrate solution for β-Galactisidose labeled antibodies includes, but is not limited to, 5-bromo-4-chloro-3-indolyl-β-D-galactopyranoside. A typical substrate solution for glucose oxidase labeled antibodies includes, but is not limited to, t-nitroblue tetrazolium chloride and m-phenazine methosulfonate.

In addition to enzyme substrate, the second solution also can include a second polyol which is operable to bind phosphate ions generated as the result of contact between alkaline phosphatase and substrate. The second polyol provides an additional means with which to decrease assay incubation periods. Typical polyols used in the substrate solution include, but are not limited to, propylene glycol, ethane glycol, butane diol, 2-amino-2-methyl-1,3-propandiol, and 2-amino-2-methyl-1-propanol with 2-amino-2-methyl-1-propanol being preferred.

Additionally, the antibodies can be labelled with a direct label. Since direct labels, unlike enzyme labels, produce visually discernable signals by virtue of their concentration and not by way of a chemical interaction, the incorporation of casein or bovine serum albumin in non-indicia areas of the test zone is generally all that is necessary to produce a differential between indicia and non-indicia on the test zone. In addition the dipstick need not be incubated a second time in substrate solution. Examples of direct labels include, but are not limited to metal sols, non-metal sols, dye sols, latex particles, carbon sol, and liposome contained colored bodies.

The component which is immobilized onto the test zone in an indicia forming configuration is either an antibody, antigen, or hapten, although either component of any ligand-receptor interaction can be employed. The antibodies used can be monoclonal or polyclonal in origin, the production methods of which are well known in the art. The antigens and haptens can be either natural or synthetic and are available from commercial sources. In addition, the immunological components can be attached to the test zone via linking reagents which have been immobilized onto the zone in the indicia forming areas. Examples of typical linking reagents include, but are not limited to, avidin, biotin, anti-flourescein antibody, and protein A.

The assay device is used in the detection of antibodies, antigens, or haptens. Examples of antibodies which may be detected using this device include, but are not limited to those to Lymes disease, cytomegalovirus, Epstein Barr virus, hepatitis, and Acquired Immune Deficiency Syndrome. Examples of antigens which may be detected using this device include, but are not limited to, human chorionic gonadotropin, luteinizing hormone, and α-fetoprotein. Examples of haptens which may be detected include, but are not limited to cocaine, tetrahydrocannabinol, digoxin, theophylline, morphine, and amphetamine.

Additionally, the present invention can be used in genetic screening and research to detect specific gene sequences by way of immobilized complement sequences and enzyme labeled DNA probes. The methods of gene sequence detection are known in the art.

The following examples will serve to further typify the nature of this invention but should not be construed as a limitation on the scope thereof, which is defined solely by the appended claims.

EXAMPLE 1

A. Dipstick Preparation. A test zone is prepared by attaching a sample (0.5 inch) of preactivated nylon membrane (Pall Immunodyne) with a pore size of 0.45 µm to a 0.01 inch thick plastic sheet (18 cm by 9 cm) serving as the base. The membrane is sprayed with 36 µl of 3 mg/ml sheep anti-human chorionic gonadotropin antibody in phosphate buffer solution (pH 7.4) along a line approximately 7–8 mm from the bottom using a Linomat IV (Camag). The sheet is incubated in phosphate buffer solution (pH 7.4) containing 2% dried milk (Carnation) and 0.5% polyvinylalcohol (MW 10,000) for 30 minutes. The sheet is washed with 5% sucrose solution, air dried, cut into strips (0.4 to 0.7 cm) to produce a series of like dipsticks which can be stored in a desiccator at ambient temperature.

B. Enzyme-Antibody Conjuingate Preparation. Alkaline phosphatase (specific activity >1400 U/mg) is coupled to monoclonal mouse anti-human chorionic gonadotropin at a 1:1 molar ratio using the one step glutaraldehyde method. The conjugate is purified on a diethylaminoethyl Sephadex A50 (5 ml) column using a linear gradient (0–1M sodium chloride) in 10 mM Tris (pH 7.4) and 5 mM magnesium chloride. Conjugate samples (3.0 ml) are collected; assayed for enzyme activity; diluted to the concentration of 1 unit/ml in 10 mM Tris (pH 7.4), 1% bovine serum albumin, 150 mM sodium chloride, and 0.1% sodium azide; and stored at 4° C.

The conjugate is aliquoted into test tubes (10×75 mm) and lyophilized. The tubes are stoppered and stored.

C. Substrate Preparation. Into additional test tubes (10×75 mm) is aliquoted 0.8 ml of 5-bromo-4-chloro indolyl phosphate-nitroblue tetrazolium substrate solution. The tubes are stored in the dark at ambient temperature.

D. Assay Performance. To a tube containing conjugate is added 1.0 ml of urine standard containing 100 mIU/ml of 100 µl human chorionic gonadotropin. The contents of the tube are mixed and the dipstick is inserted and allowed to stand for 4 minutes. The dipstick is removed and, without washing, inserted into a tube containing substrate solution and the tube is shaken. The tube is allowed to stand for an additional 4 minutes. The dipstick is removed from the tube and observed. The entire test zone is slightly off color and there is a discernable blue horizontal line across its surface. Assay sensitivity is measured to be 12 mIU/ml human chorionic gonadotropin.

EXAMPLE 2

The same procedure as Example 1(A), 1(B), 1(C), and 1(D) is followed except that in 1(D) the dipstick is initially inserted into a tube containing only urine and the conjugate; i.e., no gonadotropin. After 4 minutes the dipstick is removed, and without washing inserted into a tube of substrate solution, incubated an additional 4 minutes, and observed. The entire test zone is slightly off color but there is no discernable line across its surface.

EXAMPLE 3

The same procedures as Example 1(A), 1(B), 1(C), and 1(D) are followed except that in 1(A) the membrane is sprayed with anti-mouse immunoglobin along an additional line approximately 9-11 mm from the bottom.

The entire test zone turned slightly off color and 2 discernable blue horizontal lines formed across its surface.

EXAMPLE 4

The same procedure as Example 3 is followed except that the dipstick is initially inserted into a tube which contained only urine and the conjugate, i.e. no gonadotropin.

The entire test zone turned slightly off color and only one discernable blue horizontal line (control) formed across its surface.

EXAMPLE 5

The same procedure as Example 3 is followed except that the membrane is sprayed with sheep anti-human chorionic gonadotropin along a vertical line perpendicular to and bisecting the line of anti-mouse IgG in order to form a plus (+) sign configuration.

The entire test zone turned slightly off color and a discernable blue plus (+) sign formed across its surface.

EXAMPLE 6

The same procedure as Example 5 is followed except that the dipstick is initially inserted into a tube which contained only urine and the conjugate.

The entire test zone turned slightly off color and a discernable blue minus (−) sign formed across its surface.

EXAMPLE 7

A dipstick is prepared by the same procedure as Example 1(A) except that anti-human luteinizing hormone (LH) is used in place of anti-human chorionic gonadotropin.

Four membranes (Pall Immunodyne) are line sprayed with anti-human luteinizing hormone in accordance with the method in Example 1(A). Each membrane is then soaked in a tube of urine containing human luteinizing hormone at a given concentration (40 mIU/ml, 70 mIU/ml, 120 mIU/ml, and 200 mIU/ml). At 40 mIU/ml a slight blue band appeared on the membrane, at 70 mIU/ml a blue band of moderate intensity, at 120 mIU/ml a strong blue band, and at 200 mUI/ml a very strong blue band. A standard color chart is prepared by arranging these results in color intensity progression on a solid support.

The dipstick is inserted into a tube containing a clinical sample of urine and, without washing, into a tube of substrate solution. A moderate blue line appears on the surface of the test zone. The dipstick is compared to the color chart and it is determined that the sample contains from 40-70 mIU/ml luteinizing hormone.

EXAMPLE 8

A. Preparation of Device. A dipstick is prepared in accordance with the procedure in Example 1(A) except that the membrane is line sprayed 7-8 mm from the bottom with polyclonal anti-fluorescein isothiocyanate instead of anti-human chorionic gonadotropin. A control line is sprayed with a solution of avidin approximately 9-12 mm from the bottom of the membrane.

The dipstick test zone then is blocked by soaking in phosphate buffer solution (pH 7.4) containing 2% dried milk (Carnation) and 0.5% polyvinylacetate (MW 10,000) for 30 minutes. It then is rinsed with 5% sucrose solution, air dried, and stored in a desiccator at ambient temperature.

B. Preparation of Fluorescein Isothiocyanate-Alkaline Phosphatase Conjugate (>1400 U/ml). Twenty five microliters of fluorescein isothiocyanate in 0.10M sodium borate (pH 9.3) solution (3 mg/400 µl) is added to 5 mg of alkaline phoshatase in sodium borate at a total volume of 0.5 ml. The resultant solution is allowed to stand for 3 hours at ambient temperature.

The solution is then separated on a G25 Sephadex column and eluted with 0.1M sodium carbonate (pH 8.5). To this is added 100 ml of a solution of 5.0 mg N-hydroxysuccinimidyl biotin in 1.0 ml dimethylsulfoxide. The resultant solution is stirred for approximately 12 hours.

Free biotin is removed by separating the conjugate on a G25 Sephadex column and eluting it with a buffer containing 10 mM Tris, 1% bovine serum albumin, 150 mM sodium chloride, and 0.1% sodium azide (pH 7.4). The conjugate is then stored at 4° C.

The conjugate solution is aliquoted into 10 tubes (75 ml) and then lyophilized. The tubes are stoppered and stored.

C. Substrate Preparation. Into 10 additional tubes (75 mm) is aliquoted 0.8 ml of 5-bromo-4-chloroindolyl phosphate-nitroblue tetrazolium substrate solution. The tubes are stored in the dark at ambient temperature.

D. Competition Assay Performance. To a tube of conjugate is added 1.0 ml of urine containing fluorescein isothiocyanate (11 ng/ml). This is mixed and the dipstick is inserted and allowed to stand for 3 minutes.

The dipstick is transferred into a tube containing substrate and the tube is mixed by shaking. This is allowed to stand for 2 minutes. A dark line appears on the test zone in the control area and a faint line appears in the anti-fluorescein isothiocyanate band.

EXAMPLE 9

The same procedures as Example 8(A), 8(B), 8(C), and 8(D) are followed except that in 8(D) the dipstick is initially inserted into a tube containing only urine and the conjugate, i.e. no fluorescein. isothiocyanate. Two very dark lines appear on the test zone.

EXAMPLE 10

A. Dipstick Preparation. A test zone is prepared by attaching a sample (0.5 inch) of preactivated nylon membrane (Pall Immunodyne) with a pore size of 0.45 µm is to a 0.01 inch thick plastic sheet (18 cm by 9 cm). A band is printed onto the membrane by air-brushing 36 µl of 3 mg/ml sheep anti-human chorionic gonadotropin antibody in phosphate buffer solution along a line approximately 4 mm from the bottom. A second control band of sheep anti-mouse antibody is printed in the same way approximately 7 mm from the bottom of the membrane. The membrane is then allowed to air dry at ambient temperature for 15 hours.

B. Membrane Blocking. A solution is prepared from 5 mM of p-nitrophenyl phosphate and 0.2% polyvinylalcohol (MW 10,000) in 20 mM diethanolamine hydrochloride buffer (pH 8.5) containing 5 mM of magnesium chloride. The membrane is soaked in this solution for 30 minutes at ambient temperature, rinsed with 5% sucrose solution, air dried, cut into strips (5 mm), and stored in a desiccator at ambient temperature.

C. Enzyme-Antibody Conjugate Preparation. Alkaline phosphatase (specific activity >1400 U/mg) is coupled to monoclonal mouse anti-human chorionic gonadotropin at a 1:1 molar ratio using a one step glutaraldehyde method. The conjugate is purified on a diethylaminoethyl SEPHADEX A50 (5 mL) column using a linear gradient (0–1M sodium chloride) in 10 mM Tris (pH 7.4) and 5 mM magnesium chloride. Conjugate samples (3.0 ml) are collected; assayed for enzyme activity; diluted to 1 unit/ml in 10 mM Tris (pH 7.4), 1% bovine serum albumin, 150 mM sodium chloride, and 0.1% sodium azide; and stored at 4° C.

The conjugate is aliquoted into test tubes (10×75 mm) and lyophilized. The tubes are stoppered and stored.

D. Substrate Preparation. Into additional test tubes (10×75 mm) is aliquoted 0.8 ml of a solution containing 5-bromo-4-chloroindolyl phosphate-nitroblue tetrazolium in 2-amino-2-methyl-1-propanol. The tubes are stored in the dark at ambient temperature.

E. Assay Performance. To a tube containing conjugate is added 1.0 ml of urine standard containing 100 mIU/ml of human chorionic gonadotropin. The contents of the tube are mixed, the dipstick is inserted and allowed to stand for 4 minutes. The dipstick is removed and inserted, without washing, into a tube containing substrate solution and allowed to remain there for an additional 4 minutes. In about 30 seconds the entire test zone turned slightly off color and two dark blue lines began to appear on the test zone surface. Assay sensitivity is measured to be 12 mIU/ml.

EXAMPLE 11

The same procedures as Example 10(A), 10(B), 10(C), 10(D), and 10(E) are followed except that in 10(E) the dipstick initially is inserted into a tube containing only urine and the conjugate, i.e. no gonadotropin. After 4 minutes, the dipstick is removed and, without washing inserted into a substrate tube, incubated an additional 4 minutes, and observed. After 30 seconds the entire test zone turned slightly off color but only one dark blue line began to appear on the test zone surface.

EXAMPLE 12

A number of dipstick devices were prepared in accordance with Examples 10(A) and 10(B) except that in 10(B) each membrane was soaked in one of the following reagent combinations.

1. Milk (2%) in a 10 mM phosphate buffer solution (pH 7.5) of 150 mM sodium chloride and 0.1% sodium azide.
2. Milk (2%) in 10 mM triethanolamine hydrochloride buffer (pH 8.0).
3. Polyvinylalcohol (0.5%) in a 20 mM phosphate buffer solution (pH 7.5) of 150 mM sodium chloride and 0.1% sodium azide.
4. Polyvinylalcohol (0.5%) in 20 mM Tris buffer (pH 8.0).
5. Polyvinylalcohol (0.5%) in 20 mM borate buffer (pH 8.5).
6. Polyvinylalcohol (0.1%) and 0.1% milk in 20 mM carbonate buffer solution (pH 8.0).
7. Polyvinylalcohol (0.1%) in 20 mM 2-amino-2-methyl-2-propanol buffer solution (pH 8.5).
8. 5 mM p-nitrophenyl phosphate and 0.2% polyvinylalcohol in a 20 mM diethanolamine hydrochloride buffer solution (pH 8.5) containing 5 mM magnesium chloride.
9. 5 mM p-nitrophenyl phosphate and 0.2% polyvinylalcohol in a 20 mM diethanolamine hydrochloride buffer solution (pH 8.0).
10. Polyvinylalcohol (0.1%), Milk (0.1%), and phenylalanine (0.5%) in triethanolamine (pH 8.0).
11. Polyvinylalcohol (0.1%) and Milk (2%) in 20 mM borate buffer solution (pH 8.5).
12. Polyvinylalcohol (0.1%) and ethylene glycol (1%) in phosphate buffer solution.
13. Sorbitol (5%) and polyvinylalcohol (0.1%) in 20 mM triethanolamine (pH 8.0).
14. Corn starch (5%) and 0.1% polyethylene glycol (MW 6000).
15. Bovine serum albumin (0.1%) in Tris buffer.
16. 20 mM Tris buffer (pH 8.0).
17. 20 mM Glycine in 20 mM Tris buffer (pH 8.0).
18. Water
19. Casein (0.3%) in phosphate buffer solution.
20. No blocking solution.

The assay signal:noise ratio for the compositions are as follows (the lower the number the better the ratio).

TABLE 1

| BLOCKING SOLUTION | BACKGROUND COLOR | SIGNAL STRENGTH | COMBINED RESULT |
| --- | --- | --- | --- |
| #1 | light | weak | 6 |
| 2 | light | weak | 6 |
| 3 | moderate | moderate | 6 |
| 4 | light | very strong | 3 |
| 5 | light | very strong | 3 |
| 6 | light | weak | 6 |
| 7 | light | strong | 4 |
| 8 | very light | very strong | 2 |
| 9 | light | strong | 4 |
| 10 | moderate | moderate | 6 |
| 11 | moderate | moderate | 6 |
| 12 | moderate | very weak | 8 |
| 13 | moderate | very weak | 8 |
| 14 | moderate | strong | 5 |
| 15 | very dark | weak | 9 |
| 16 | very dark | weak | 8 |
| 17 | moderate | weak | 7 |
| 18 | dark | very weak | 9 |
| 19 | very light | strong | 3 |
| 20 | very dark | very weak | 10 |

EXAMPLE 13

The same procedures as Example 10(A), 10(B), 10(C), 10(D), 10(E) are followed except that in 10(A) the membrane is sprayed with the sheep anti-human chorionic gonadotropin along a vertical line perpendicular to and bisecting the line of anti-mouse IgG in order to form a plus (+) sign configuration. In about 30 seconds the entire test zone turned slightly off color and a dark blue plus (+) sign began to appear on the test zone surface.

EXAMPLE 14

The same procedure as Example 13 is followed except that the dipstick is initially inserted into a tube which contained only urine and the conjugate, i.e. no gonadotropin.

The entire test zone turned slightly off color and a very dark blue minus (−) sign formed across its surface.

EXAMPLE 15

The dipstick is prepared by the same procedure as Example 10(A) except that anti-human luteinizing hormone (LH) is used in place of anti-human chorionic gonadotropin and there is no control band.

Four membranes (Pall Immunodyne) are line sprayed with anti-human luteinizing hormone in accordance with the method in Example 10(A). Each membrane is then dipped into a tube of urine containing human luteinizing hormone at a given concentration (40 mIU/ml, 70 mIU/ml, 120 mIU/ml, and 200 mIU/ml). At 40 mIU/ml a slight but very distinct blue band appeared on the membrane, at 70 mIU/ml a very distinct blue band of moderate intensity, at 120 mIU/ml a very distinct strong blue band, and at 200 mUI/ml a very distinct and very strong blue band. A standard color chart is prepared by arranging these results in order of color intensity on a solid support.

The dipstick is inserted into a tube containing a clinical sample of urine and without washing into a tube of substrate solution. A very distinct strong blue line appears on the surface of the test zone. The dipstick is compared to the color chart and it is determined that the sample contains from 120–200 mIU/ml luteinizing hormone.

EXAMPLE 16

The dipstick is prepared by the same procedure as Example 10(A) except that anti-human luteinizing hormone (LH) is used in place of anti-human chorionic gonadotropin and the control band is printed with anti-mouse antibody in the concentration of 40 mIU/ml.

The dipstick is inserted into a tube containing a clinical sample of urine allowed to incubate for 4 minutes, removed, and then inserted without washing into the substrate solution. Two distinct blue lines appear on the surface of the test zone. The second line is darker than the control line indicating the presence of greater than 40 mIU/ml of luteinizing hormone in the sample.

EXAMPLE 17

A. Preparation of Device. A dipstick is prepared in accordance with the procedure in Example 10(A) except that the membrane is line sprayed 7–8 mm from the bottom with polyclonal anti-fluorescein isothiocyanate instead of anti-human chorionic gonadotropin. The control line is sprayed with a solution of avidin approximately 9–12 mm from the bottom of the membrane.

B. Preparation of Fluorescein isothiocyanate-Alkaline Phophatase. Conjugate (>1400 U/ml). Twenty five microliters of fluorescein isothiocyanate in 0.10M sodium borate (pH 9.3) solution (3 mg/400 µl) is added to 5 mg of alkaline phoshatase in sodium borate at a total volume of 0.5 ml. The resultant solution is allowed to stand for 3 hours at ambient temperature.

The solution is then separated on a G25 SEPHADEX column and eluted with 0.1M sodium carbonate (pH 8.5). To this is added 100 ml of a solution of 5.0 mg N-hydroxysuccinimidyl biotin in 1.0 ml dimethylsulfoxide. The resultant solution is stirred for approximately 12 hours.

Free biotin is removed by separating the conjugate on a G25 SEPHADEX column and eluting it with a buffer containing 10 mM Tris, 1% bovine serum albumin, 150 mM sodium chloride, and 0.1% sodium azide (pH 7.4). The conjugate is then stored at 4° C.

The conjugate solution is aliquoted into 10 tubes (75 ml) and then lyophilized. The tubes are stoppered and stored.

C. Substrate Preparation. Into 10 additional tubes (75 mm) is aliquoted 0.8 ml of 5-bromo-4-chloro indolyl phosphate-nitroblue tetrazolium substrate solution. The tubes are stored in the dark at ambient temperature.

D. Competition Assay Performance. To a tube of conjugate is added 1.0 ml of urine containing fluorescein isothiocyanate (11 ng/ml) and the dipstick. This is mixed and allowed to stand for 3 minutes.

The device is then without washing moved into a tube containing substrate and the tube is mixed by shaking. This is allowed to stand for 2 minutes. A dark line appears on the test zone in the control area and a faint line appears in the anti-fluorescein isothiocyanate band.

EXAMPLE 18

The same procedure as Example 17 is followed except that the dipstick is initially inserted into a tube containing only urine and the conjugate, i.e. no gonadotropin. Two very dark lines appear on the test zone.

What is claimed is:

1. A dipstick immunoassay device comprising:

a base member;

a single, combined sample contact zone and test zone, defined on said base member, said test zone including a control indicia portion, a test indicia portion and a non-indicia portion;

a first immobilized immunological component being disposed solely in said control indicia portion, said first immunological component being an anti-immunoglobulin which is capable of binding to an enzyme-labeled antibody, said enzyme-labeled antibody producing a visual color differential between said control indicia portion and said non-indicia portion upon contact with a substrate;

a second immobilized immunological component being disposed solely in said test indicia portion, said second immunological component being capable of specifically binding to a target analyte which is bound to said enzyme-labeled antibody to form a sandwich complex, said enzyme-labeled antibody producing a visually discernable difference between said indicia portions and said non-indicia portion, upon contact with a substrate;

a first polyol distributed throughout said non-indicia portion of said test zone; and a color differential enhancing component selected from the group consisting of an inhibitor to said enzyme and a competitive secondary substrate for said enzyme, said component distributed throughout said non-indicia portion of said test zone.

2. The assay device according to claim 1 wherein said second immobilized component is an antibody, antigen or hapten.

3. The assay device according to claim 2 wherein said second immobilized component is an antibody.

4. The assay device according to claim 1 wherein said enzyme is alkaline phosphatase, horse radish peroxidase, lysozyme, glucose-6-phosphate dehydrogenase, lactate dehydrogenase, urease, glucose oxidase, or cholesterol oxidase.

5. The assay device according to claim 4 wherein said enzyme is alkaline phosphatase.

6. The assay device according to claim 1 wherein said enzyme inhibitor is an amino acid or a metal chelator.

7. The assay device according to claim 1 wherein said inhibitor is selected from the group consisting of cysteine, histidine, L-phenylalanine, β-phenyl-β-alanine, p-fluorophenylalanine, tyrosine, iodobenzoate, iodoacetamide, citrate, ethylene diamine tetraacetic acid, borate, arsenate, phosphate, orthophosphate, carbonate, polyestradiol phosphate, pyrophosphate, and polyphloretin phosphate.

8. The assay device according to claim 1 wherein said competitive secondary substrate is p-nitrophenyl phosphate.

9. The assay device according to claim 1 wherein the target analyte is an antigen, an antibody, or a hapten.

10. The assay device according to claim 1, wherein said test indicia portion and said control indicia portion are each in the form of a bar or a dot.

11. The assay device according to claim 1 wherein said base member is comprised of a member selected from the group consisting of plastic and glass.

12. The assay device according to claim 1 wherein said test zone is comprised of a member selected from the group consisting of nylon, nitrocellulose, cellulose, fiberglass, polysulfone, polyvinylidene difluoride, and polyester.

13. The assay device according to claim 1 wherein said second immunological component is an antibody specific for said analyte and being conjugated to alkaline phosphatase and said inhibitor is a member selected from the group consisting of cysteine, histidine, L-phenylalanine, β-phenyl-β-alanine, p-fluorophenylalanine and tyrosine.

14. A dipstick immunoassay device comprising:
   a base member;
   a single, combined sample contact zone and test zone, defined on said base member, said test zone including a control indicia portion, a test indicia portion and a non-indicia portion;
   a first immobilized antibody being disposed solely in said control indicia portion, said first immobilized antibody being an anti-immunoglobulin antibody which is capable of binding to an alkaline phosphatase-labeled antibody, said alkaline phosphatase-labeled antibody producing a visual color differential between said control indicia portion and said non-indicia portion upon contact with a substrate;
   a second immobilized antibody being disposed solely in said test indicia portion, said second antibody being capable of specifically binding to a target analyte which is bound to said alkaline phosphatase-labeled antibody to form a sandwich complex, said alkaline phosphatase-labeled antibody producing a visually discernable difference between said indicia portions and said non-indicia portion, upon contact with a substrate;
   a first polyol distributed throughout said non-indicia portion of said test zone; and
   a color differential enhancing component selected from the group consisting of an inhibitor to said alkaline phosphatase and a competitive secondary substrate for said alkaline phosphatase, said component distributed throughout said non-indicia portion of said test zone.

15. The assay device according to claim 14 wherein said inhibitor is an amino acid or a chelating agent.

16. The assay device according to claim 14 wherein said inhibitor is cysteine, histidine, L-phenylalanine, β-phenyl-β-alanine, p-fluorophenylalanine, tyrosine, iodobenzoate, iodoacetamide, ethylenediamine tetraacetic acid, citrate, orthophosphate, arsenate pyrophosphate, borate, carbonate, polyestradiol phosphate, polyphloretin phosphate or phosphate.

17. The assay device according to claim 14 wherein said competitive secondary substrate is p-nitrophenyl phosphate.

18. The assay device according to claim 14 wherein the target analyte is an antigen, an antibody, or a hapten.

19. The assay device according to claim 14 wherein said base member is comprised of a member selected from the group consisting of plastic and glass.

20. The assay device according to claim 14 wherein said test zone is comprised of a member selected from the group consisting of nylon, nitrocellulose, cellulose, fiberglass, polysulfone, polyvinylidene difluoride, and polyester.

21. The assay device according to claim 14 wherein said first polyol is polyvinylalcohol, carbohydrate, polyethylene glycol, sorbitol, polypropylene glycol, dextran, methyl cellulose, milk, or corn starch.

22. The assay device according to claim 14 wherein said first polyol is polyvinylalcohol.

23. The assay device according to claim 14, wherein said test indicia portion and said control indicia portion are each in the form of a bar or a dot.

24. A kit comprising
   an assay device according to claim 14;
   a first solution comprising alkaline phosphatase labeled antibody; and
   a second solution comprising a substrate operable to form an insoluble colored product and phosphate ions upon contact with said alkaline phosphatase and a second polyol operable to bind said phosphate ions.

25. The kit according to claim 14 wherein said second polyol is propylene glycol, ethane glycol, 2-amino-2-methyl-1-propanol, or butane diol.

26. The kit according to claim 25 wherein said second polyol is 2-amino-2-methyl-1-propanol.

* * * * *